United States Patent [19]

Noyes et al.

[11] Patent Number: 6,022,356
[45] Date of Patent: Feb. 8, 2000

[54] CRUCIATE LIGAMENT RECONSTRUCTION TEMPLATE

[75] Inventors: Frank R. Noyes, Cincinnati, Ohio; Paul A. Torrie, Marblehead, Mass.

[73] Assignee: Smith & Nephew, Inc., Andover, Mass.

[21] Appl. No.: 09/040,534

[22] Filed: Mar. 18, 1998

[51] Int. Cl.[7] .................................................. A61B 17/58
[52] U.S. Cl. .............................................. 606/96; 606/88
[58] Field of Search .......................... 606/96, 87, 88, 606/102; 408/241 G

[56] References Cited

U.S. PATENT DOCUMENTS 5,462,549  10/1995  Glock ........................................ 606/88
5,769,856  6/1998  Dong et al. ................................ 606/96

OTHER PUBLICATIONS

Anatomic Femoral Tunnel Placement 6.0 (pp. 12–13) (undated, published prior to Mar. 18, 1998).

*Primary Examiner*—Michael Buiz
*Assistant Examiner*—Julian W. Woo
*Attorney, Agent, or Firm*—Fish & Richardson P.C.

[57] ABSTRACT

A template for use in forming an insertion for cruciate ligament reconstruction surgery includes a template body that is inserted into the knee and positioned on a wall of the femoral notch of the knee. The template body includes openings sized and positioned to receive guidewires and to direct the guidewires into the wall of the femoral notch.

31 Claims, 7 Drawing Sheets

CRUCIATE LIGAMENT RECONSTRUCTION TEMPLATE

TECHNICAL FIELD

The invention relates to positioning a femoral insertion during posterior cruciate ligament (PCL) or anterior cruciate ligament (ACL) reconstruction surgery.

BACKGROUND INFORMATION

The PCL and ACL are attached between the tibia and the femur in the knee. In cruciate ligament reconstruction surgery, a damaged cruciate ligament is replaced with a tendon graft or artificial graft that is secured to the tibia and the femur.

A known technique for securing a PCL graft to the femur involves drilling a femoral tunnel from outside the joint, through the femur, and into the central notch of the femur. An aimer arm of a guide, such as an ACL guide with a dedicated PCL aimer, is placed through a portal of the knee with the point of the aimer arm located where the tunnel will enter the notch. The other end of the guide has an advanceable guidewire support tube (bullet) that is positioned against the exterior of the femur through a small incision. The guide assures that a guidewire inserted through the bullet will pass through the femur and hit the aimer point.

The position of the aimer point may be viewed arthroscopically, and a series of depth marks are provided on the aimer arm for use in positioning the aimer point on the notch wall. These depth marks indicate the distance from the aimer point to the intersection of the notch wall and articular cartilage.

SUMMARY

In one general aspect, the invention features a template for use in forming an insertion for cruciate ligament reconstruction surgery. As used throughout this document, the term "insertion" refers to the one or more cavities or tunnels used to secure a cruciate ligament graft to the femur. An insertion may include a single cavity or a collection of cavities.

The template includes a template body configured to be inserted into a knee and positioned on a wall of a femoral notch of the knee. The template body includes openings sized and positioned to receive guidewires and to direct the guidewires into the wall of the femoral notch.

Embodiments may include one or more of the following features. A shape of the template body may generally correspond to a desired shape of a cruciate ligament insertion.

The openings may be defined as recesses in a perimeter of the template body. The recesses may be defined so that the guidewires are removable through the perimeter of the template body. The recesses may include narrowed portions having widths slightly smaller than the diameters of the guidewires so that the guidewires are maintained in the recesses until a force sufficient to deform the guidewires or the template body is applied to remove the guidewires through the perimeter of the template body.

An arm extending from the template body may be positioned and configured to include a portion that remains outside of the knee when the template body is inserted into the knee. Depth marks may be defined on the arm for use in positioning the template body on the wall of the femoral notch.

A handle may be connected to the arm, and a second arm may extend from a second end of the handle. A second template body may be positioned at the end of the second arm. The template bodies may be formed with opposite orientations so that the openings of the first template body are formed as recesses on a side of the first template body positioned further from the handle and the openings of the second template body are formed as recesses on a side of the second template body positioned closer to the handle. The two template bodies also may include different numbers of openings, or different spacing between the openings.

In another general aspect, the invention features forming an insertion for cruciate ligament reconstruction surgery. First, a template is inserted into a knee and positioned on a wall of a femoral notch of the knee. The template includes openings sized and positioned to receive guidewires and to direct the guidewires into the wall of the femoral notch. Guidewires then are inserted into the wall of the femoral notch using openings in the template, and holes are drilled in the wall of the femoral notch using the guidewires. The holes may be drilled after all of the guidewires are in place, or the first hole may be drilled after the first guidewire is in place, with the second guidewire being inserted after the first hole is drilled.

The template may be removed from the knee after inserting the second guidewire. The holes may be drilled using a cannulated drill bit having an opening through which a guidewire passes. The holes may be drilled from inside out (i.e., from the wall of the femoral notch), and may be drilled only a limited distance into (e.g., 2 to 2.5 centimeters), and not completely through, the femur. The holes also may be drilled from outside in, and completely through the femur.

The guidewires may be inserted through the openings in the template. Alternatively, the openings in the template may be used to mark the desired position of the guidewires by, for example, electro-cautery. The holes may be separated by a bony bridge. Alternatively, the holes may overlap. A dilator may be directed into the holes to create a cavity in the wall of the femoral notch having a desired shape.

A first portion of a ligament graft may be tensioned and attached to the first hole when the knee is in a first position and a second portion of the ligament graft may be tensioned differently and attached to the second hole when the knee is in a second, substantially different position. This more closely approximates the tension found in the PCL of a healthy knee.

In another general aspect, the invention features forming a cavity for cruciate ligament reconstruction surgery by inserting a first guidewire into a femur and inserting a second guidewire into the femur using a device, such as a parallel offset guide, configured to space the second guidewire a predetermined distance from a location defined by the first guidewire. Holes then are drilled in the femur using the guidewires. While the guidewires are inserted from outside the knee, the holes may be drilled from inside the knee, and do not need to extend all of the way through the femur.

The first hole may be drilled after inserting the first guidewire, but before inserting the second guidewire. The second guidewire may be inserted using a device configured to space the second guidewire a predetermined distance from the first hole.

The invention provides a device and techniques for accurately and repeatably placing the femoral insertion cavity during cruciate ligament reconstruction so as to reduce surgery time and increase consistency. The device may include an insertion template that permits creation of a femoral insertion cavity that closely matches the anatomic attachment of the cruciate ligament to the femur. The anatomic attachment for the PCL more closely resembles an oval or tri-oval than the circle created by prior, single tunnel techniques. To recreate the anatomic attachment more accurately, the insertion template is used to make two or more holes, or a non-circular insertion in the femur.

The template system allows for repeatable femoral footprint geometry during cruciate ligament reconstruction. By contrast, present instrumentation, such as is discussed above, addresses only the placement of a singular tunnel. The template fixes the distance between tunnels, and may be used to create a non-round footprint. It also may be used to position the footprint relative to the anatomy of the knee.

Other features and advantages of the invention will be apparent from the following detailed description, including the drawings, and from the claims.

DETAILED DESCRIPTION

Figure 1:
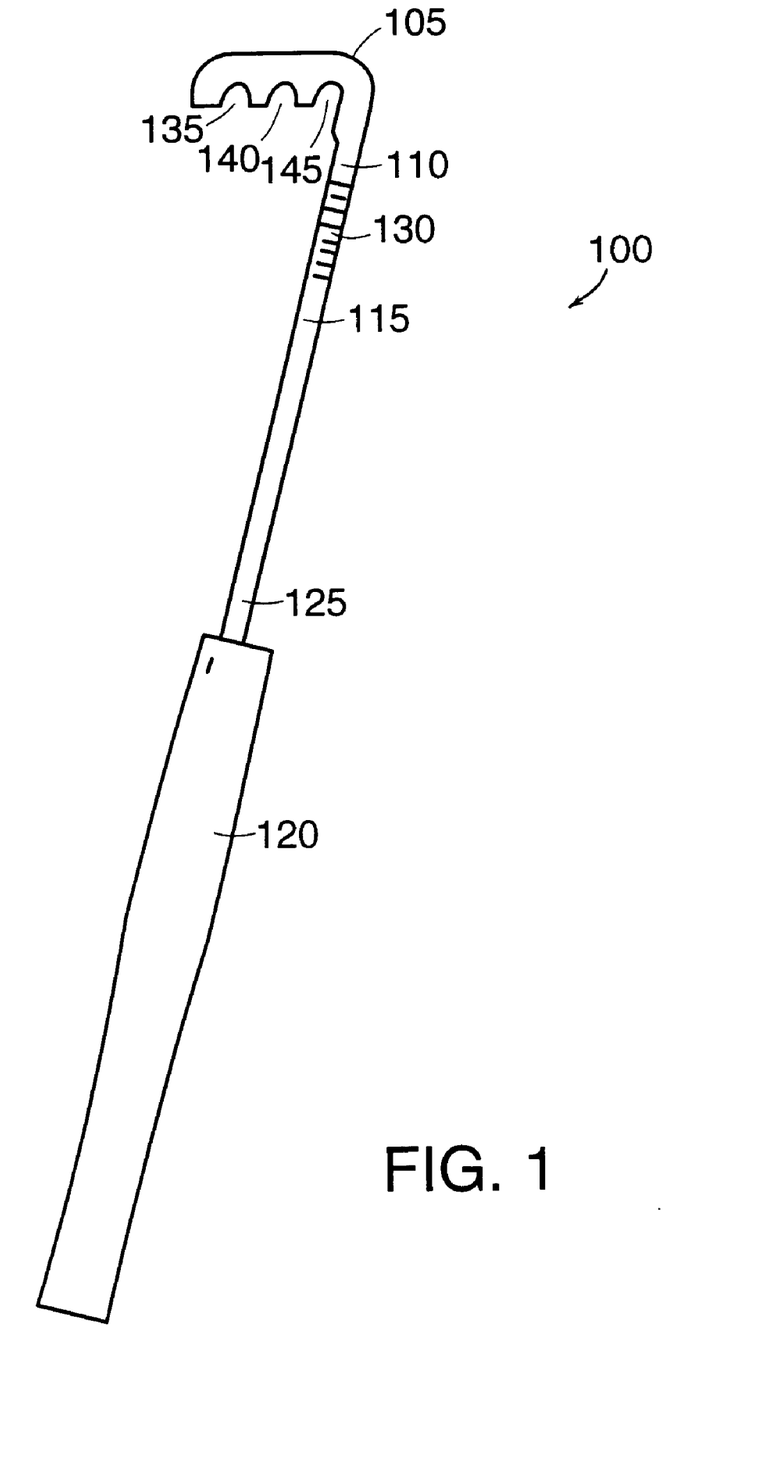
FIG. 1 is a side view of an insertion template.

Referring to FIG. 1, an insertion template 100 for creating a non-circular insertion cavity or multiple holes includes a template body 105 positioned at a distal end 110 of a shaft 115. A handle 120 is positioned at the proximal end 125 of the shaft 115. The handle 120 is generally cylindrical in shape and is sized to be grasped comfortably by the surgeon. Depth marks 130 on the shaft 115 are used in positioning the template body relative to the intersection of the wall of the femoral notch and articular cartilage.

The template body 105 is shaped to be generally representative of the insertion footprint (e.g., oval) and incorporates three recesses 135, 140 and 145 to support guidewires. The recesses are separated by a fixed distance and spaced so that positioning guidewires in recesses 135 and 145 and drilling over those guidewires permits separate insertion cavities to be formed. By contrast, drilling over guidewires positioned in recesses 135 and 140 results in a single insertion cavity that is generally oval in shape.

The template body 105 represents only part of the footprint since the template body must be removable from the guidewires after they have passed through it. Accordingly, the recesses 135–145 are open and provide passages to the perimeter of the template body. The passages may be sized to permit the template to freely slide away from the guidewires. Alternatively, the recesses may surround most, but not all, of the circumference of each guidewire. With the recesses so configured, the template is not able to slip off of the guidewires in normal use. However, when forced, the template can be "unsnapped" by the elastic deformation of the portions of the template surrounding the recesses.

Figure 2:
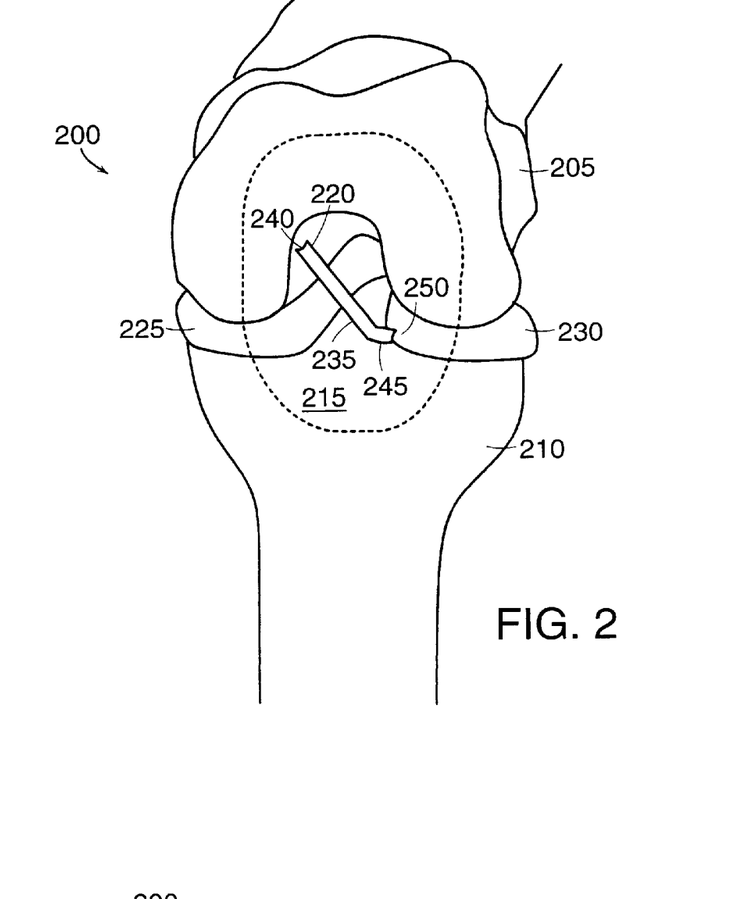
FIGS. 2 and 3 are front and side views of a knee.
Figure 3:
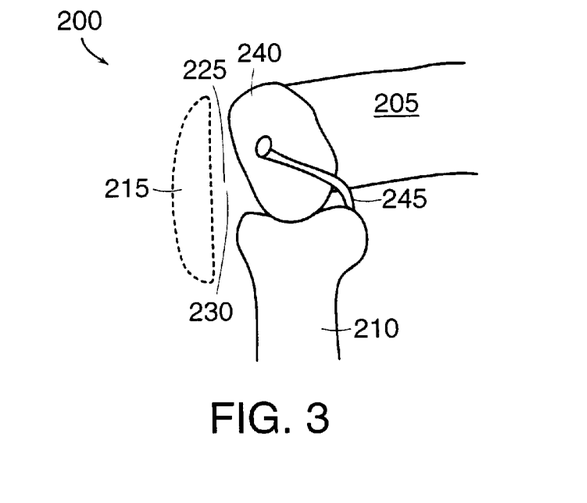

Referring to FIGS. 2 and 3, the knee 200 is defined by the femur 205, the tibia 210, and the patella 215. A central notch 220 is defined at the end of the femur 205. The region defined by the notch may be accessed through a medial portal 225 and a lateral portal 230. In a healthy knee, the PCL 235 extends from the medial side 240 of the femoral notch to a posterior point 245 behind and below the tibial plateau 250.

Figure 4A:
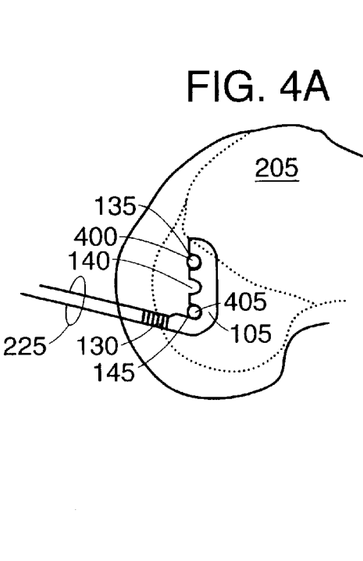
FIGS. 4A and 4B are side views showing formation of separate insertion cavities in a femur.

Referring also to FIG. 4A, template body 105 is inserted arthroscopically through the medial portal 225 and held against the notch wall. The template body 105 is viewed through an endoscope (not shown) inserted through the lateral portal 230. The endoscope provides a view comparable to the view of FIG. 4A. Anatomical landmarks and the depth marks 130 are referenced to locate the template body 105 on the wall surface.

Figure 4B:
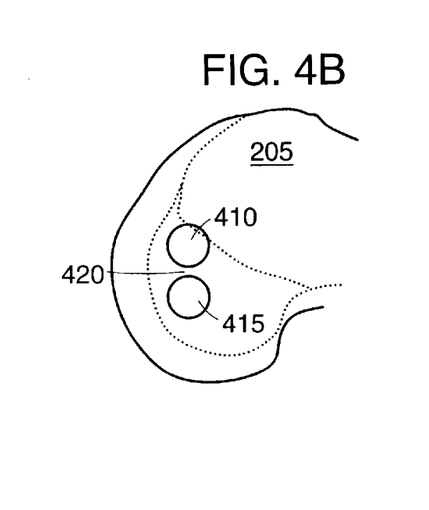

Guidewires 400 and 405 are passed through the lateral portal and inserted into the femur through recesses 135 and 145, respectively. Next, the template is removed and the guidewires are overdrilled using a cannulated drill bit inserted along each guidewire through the lateral portal. The drill bit is inserted to a desired depth (e.g., 2 to 2.5 cm), but does not pass completely through the femur. Referring to FIG. 4B, using this technique with a fixed distance between the guidewires and sufficiently small drill bit diameters results in two cavities 410 and 415 that are separated by a bony bridge 420.

Figure 5A:
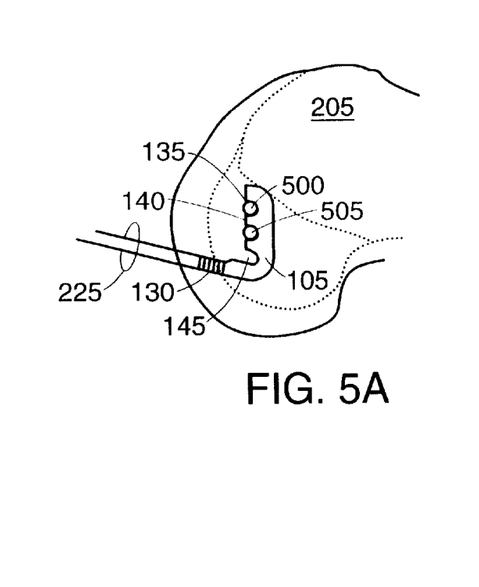
FIGS. 5A–5C are side views showing formation of overlapping insertion cavities in a femur.
Figure 5B:
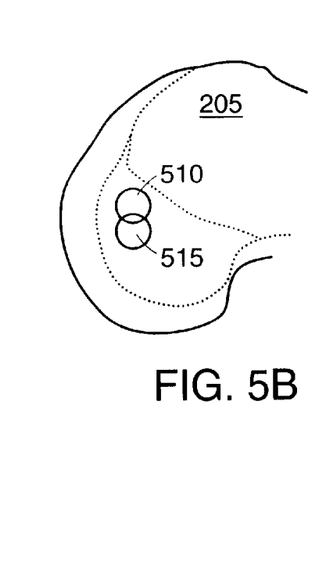
Figure 5C:
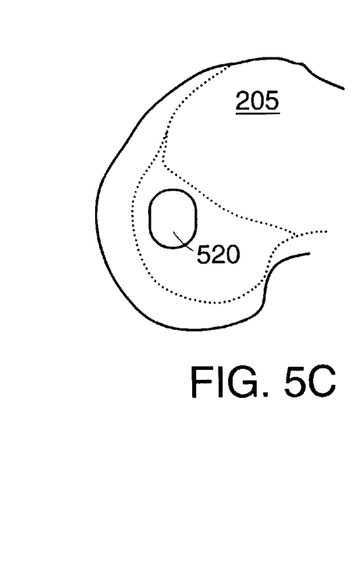

Referring to FIG. 5A, guidewires 500 and 505 may be inserted into the femur through recesses 135 and 140. Overdrilling the guidewires results in the overlapping cavities 510 and 515 shown in FIG. 5B. A dilator, such as the dilator 600 illustrated in FIG. 6, may be inserted into the overlapping cavities 510 and 515. The dilator compresses the bone away from the drilled holes to form a cavity that conforms to the shape of the end of the dilator, which may be of any desired shape (e.g., an oval or tri-oval). For example, the dilator may be shaped to form an oval cavity, such as the cavity 520 shown in FIG. 5C.

Figure 6:
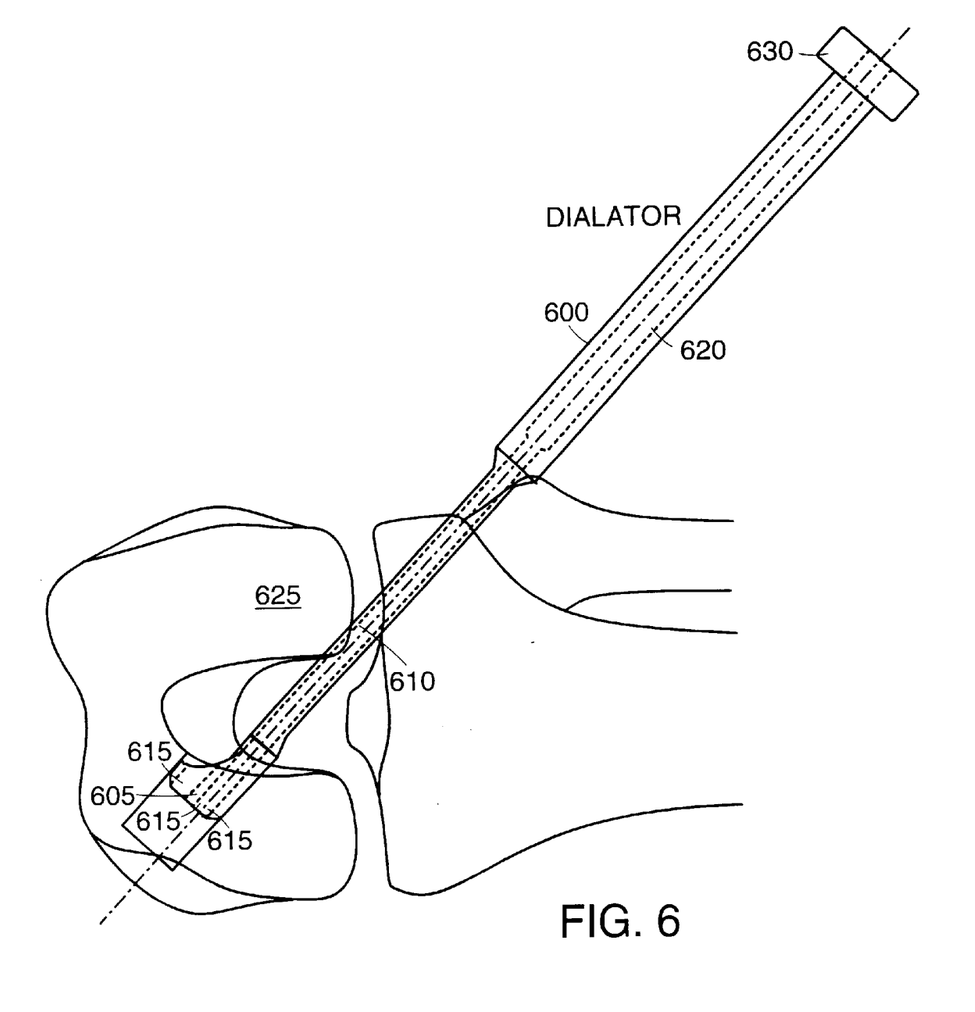
FIG. 6 is a side view of a dilator.

Referring to FIG. 6, the dilator 600 includes an head 605 connected to a tapered neck 610. The head is shaped to conform to the desired shape of the cruciate ligament insertion. For example, the head may have an oval or tri-oval shape. The head may include channels 615 sized and configured to allow implanted guidewires to pass through. The neck is connected to a handle 620. The neck is tapered and asymmetrically offset so as to not interfere with the lateral condyle 625. Finally, the handle 620 includes an expanded portion 630 that may be used to pound the dilator into or out of place.

In summary, to form two holes for reconstruction surgery, the template is inserted into the central notch of the femur. Guidewires then are inserted into the femur through the template. Next, the template is removed and the guidewires are overdrilled from the central notch into the femur to a desired depth. Alternatively, the guidewires may be overdrilled from outside the femur to form tunnels that extend completely through the femur.

Next, one end of a graft is fixated on the tibia, and the other end is fixated on the femur. The graft may be fixated using, for example, interference screws or sutures tied to screw posts. The femoral end of the graft may be separated into two strands, with each of the strands being fixated in a different hole. Advantageously, each strand may be fixated at a different flexion of the knee. For example, the top strand may be fixated and tensioned with the knee at 90° flexion while the bottom strand is fixated and tensioned with the knee fully extended.

Alternatively, the template may be used to form a cavity defined by intersecting holes, and a dilator may be used to conform the cavity to the desired footprint. The dilator, the end of which is made from solid metal with channels, is forced into the cavity. As it progresses into the cavity, the dilator compresses bone and pushes the bone to the side. In general, the shape of the dilator may be an oval or a tri-oval (i.e., a triangle with rounded corners).

Figure 7:
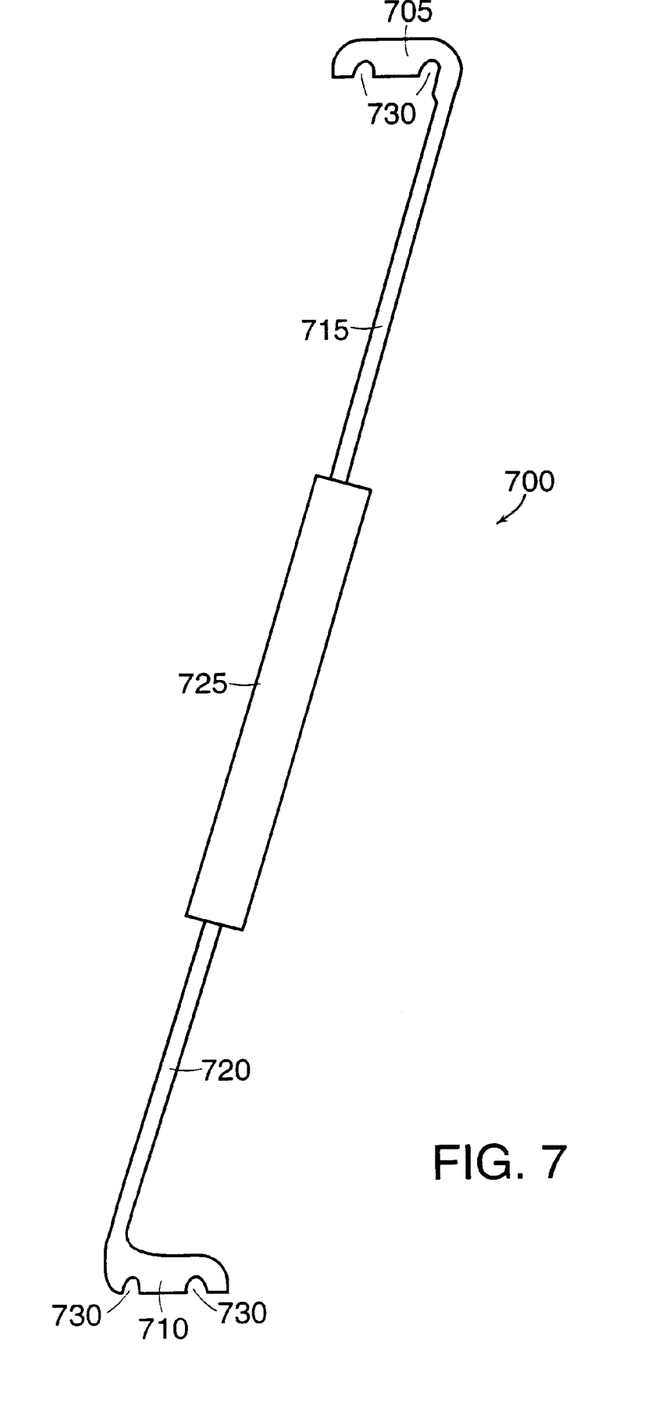
FIG. 7 is a side view of an insertion template.

Referring to FIG. 7, a template 700 may include two template bodies, with a first body 705 being configured to snap away from the guidewires in response to a pushing motion, and a second body 710 being configured to snap away from the guidewires in response to a pulling motion. These different orientations provide the surgeon with flexibility during use. The template bodies are fixed on arms 715, 720 extending from opposite ends of a handle 725. Each body includes two recesses 730 positioned relatively far from each other for making separate holes. Other combinations of dual-recess or tri-recess bodies also could be included in a dual body device.

Figures 8A, 8B:
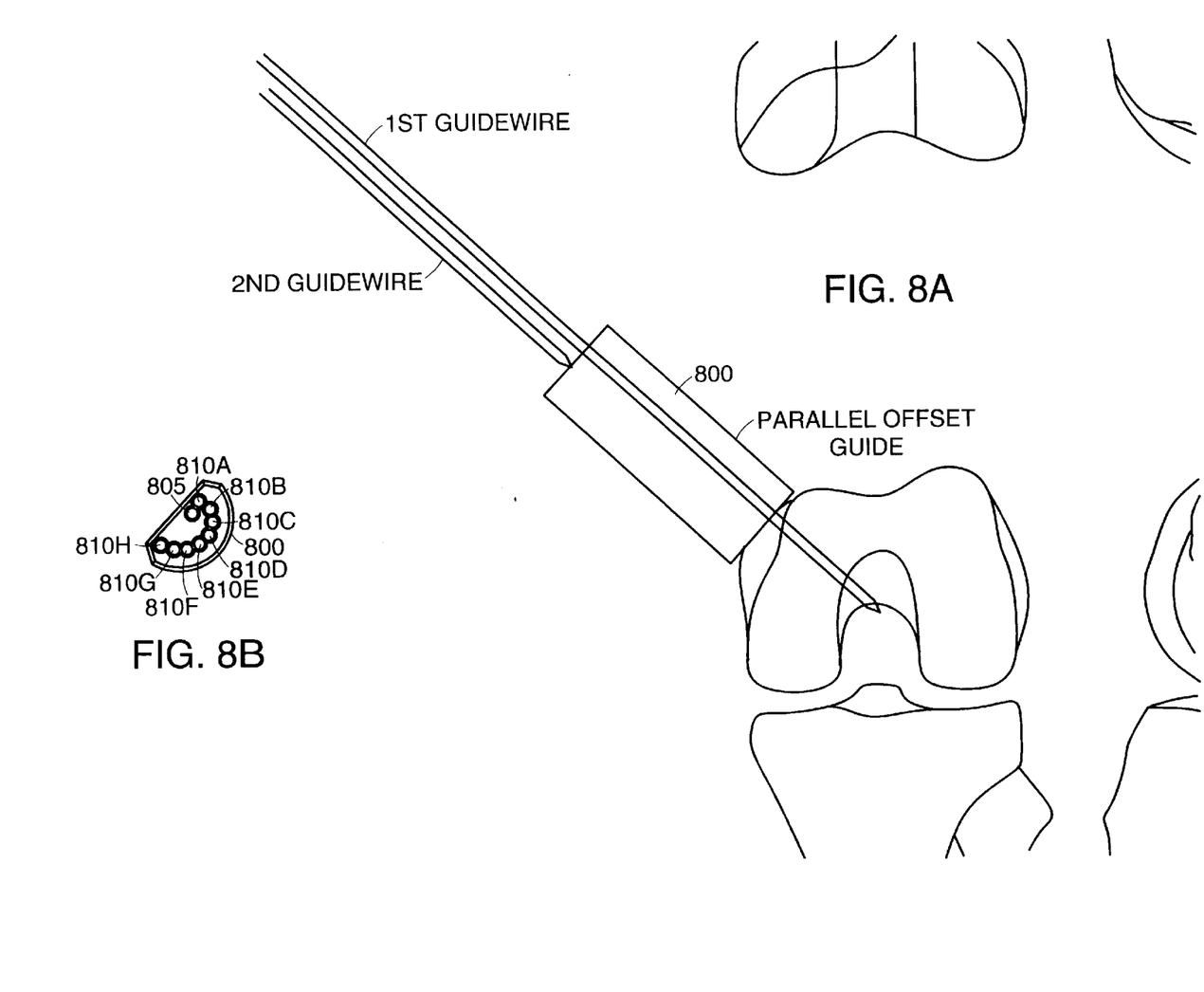
FIGS. 8A and 8B are side and end views of a parallel offset guide.

Referring to FIGS. 8A and 8B, in another implementation, a parallel offset guide 800 may be used to insert separate holes from outside the femur into the central notch. With this approach, a first guidewire is inserted into the femur using known techniques. The offset guide 800 then is positioned onto the first guidewire through hole 805 in the offset guide. A second guidewire then is inserted through a hole 810 (e.g., hole 810B) having a desired spacing from the hole 805.

Figure 9A:
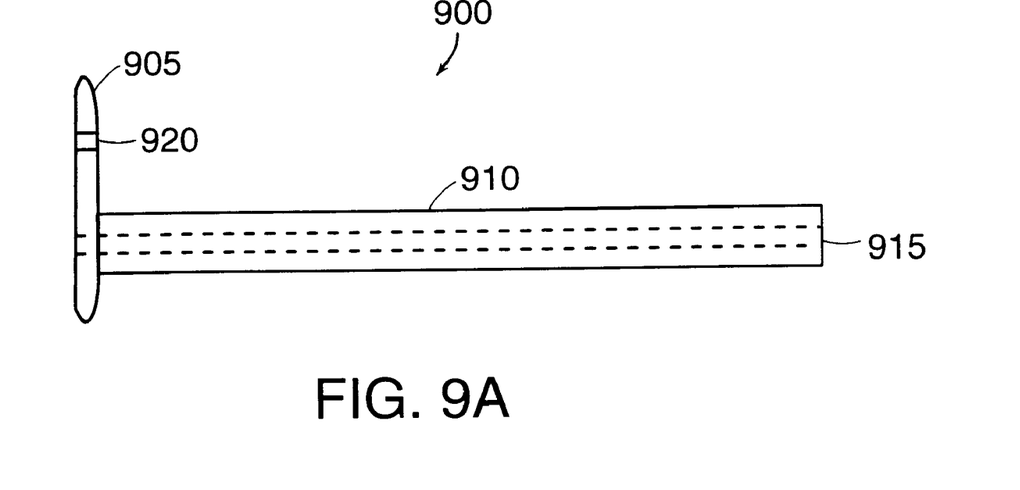
FIGS. 9A and 9B are side and end views of an insertion template.
Figure 9B:
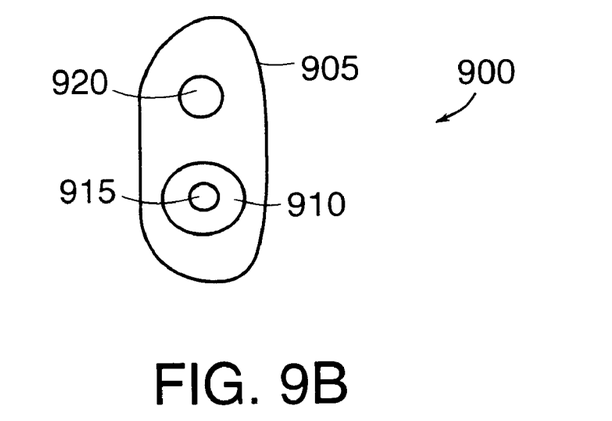

Referring to FIGS. 9A and 9B, an insertion template 900 includes a template body 905 and a handle 910. The handle 910 includes an opening 915 sized to receive a guidewire and aligned with a corresponding opening in the template body 905. The template body 905, which is generally oval in shape, includes an additional opening 920 sized to receive a guidewire. The template 900 is configured to be inserted through the portal through which the guidewires are inserted.

Other embodiments are within the scope of the following claims.

What is claimed is:

1. A template for use in forming an insertion for cruciate ligament reconstruction surgery, the template comprising a template body configured to be inserted into a knee and positioned on a wall of a femoral notch of the knee, the template body including openings sized and positioned to receive guidewires and to direct the guidewires into the wall of the femoral notch, wherein the openings are defined as recesses in a perimeter of the template body.

2. A template for use in forming an insertion for cruciate ligament reconstruction surgery, the template comprising a template body configured to be inserted into a knee and positioned on a wall of a femoral notch of the knee, the template body including openings sized and positioned to receive guidewires and to direct the guidewires into the wall of the femoral notch, wherein at least one of the openings is defined as a recess in a perimeter of the template body.

3. The template of claim 2, wherein the openings are defined as recesses in a perimeter of the template body.

4. The template of claim 1, wherein the recesses are defined so that the guidewires are removable through the perimeter of the template body.

5. The template of claim 4, wherein the recesses include narrowed portions having widths slightly smaller than the diameters of the guidewires so that the guidewires are maintained in the recesses until a force sufficient to deform the guidewires or the template body is applied to remove the guidewires through the perimeter of the template body.

6. The template of claim 1, further comprising an arm extending from the template body, the arm being positioned and configured to include a portion that remains outside of the knee when the template body is inserted into the knee.

7. A template for use in forming an insertion for cruciate ligament reconstruction surgery, the template comprising:
a template body configured to be inserted into a knee and positioned on a wall of a femoral notch of the knee, the template body including openings sized and positioned to receive guidewires and to direct the guidewires into the wall of the femoral notch;
an arm extending from the template body, the arm being positioned and configured to include a portion that remains outside of the knee when the template body is inserted into the knee; and
depth marks defined on the arm for use in positioning the template body on the wall of the femoral notch.

8. The template of claim 6, further comprising a handle connected to the arm.

9. The template of claim 8, wherein a first end of the handle is connected to the arm, the template further comprising a second arm extending from a second end of the handle.

10. A template for use in forming an insertion for cruciate ligament reconstruction surgery, the template comprising:
a template body configured to be inserted into a knee and positioned on a wall of a femoral notch of the knee, the template body including openings sized and positioned to receive guidewires and to direct the guidewires into the wall of the femoral notch;
a first arm extending from the template body, the first arm being positioned and configured to include a portion that remains outside of the knee when the template body is inserted into the knee;
a handle having a first end and a second end, the first end being connected to the first arm;
a second arm extending from a second end of the handle; and
a second template body positioned at an end of the second arm, the second template body being configured to be inserted into the knee and positioned on the wall of the femoral notch and including openings sized and positioned to receive guidewires and to direct the guidewires into the wall of the femoral notch.

11. The template of claim 10, wherein the openings of the first template body are formed as recesses on a side of the first template body positioned further from the handle and the openings of the second template body are formed as recesses on a side of the second template body positioned closer to the handle.

12. The template of claim 10, wherein the first template body includes a number of openings that differs from a number of opening included on the second template body.

13. The template of claim 10, wherein openings of the first template body are positioned closer together than are openings of the second template body.

14. A method of forming an insertion for cruciate ligament reconstruction surgery, the method comprising:
inserting a template into a knee and positioning the template on a wall of a femoral notch of the knee, the template including openings sized and positioned to receive guidewires and to direct the guidewires into the wall of the femoral notch;
inserting a first guidewire into the wall of the femoral notch using a first opening in the template;
inserting a second guidewire into the wall of the femoral notch using a second opening in the template;

drilling a first hole in the wall of the femoral notch using the first guidewire; and drilling a second hole in the wall of the femoral notch using the second guidewire.

15. The method of claim 14, further comprising removing the template from the knee after inserting the second guidewire.

16. The method of claim 15, wherein drilling the first hole comprises drilling the first hole after inserting the first guidewire and before inserting the second guidewire.

17. The method of claim 14, wherein drilling the first hole comprises using a cannulated drill bit having an opening through which the first guidewire passes.

18. The method of claim 14, wherein drilling the first hole comprises drilling the first hole from the wall of the femoral notch.

19. The method of claim 18, wherein drilling the first hole comprises drilling the first hole only a limited distance into, and not completely through, the femur.

20. The method of claim 14, wherein the first and second holes are separated by a bony bridge.

21. The method of claim 20, wherein the first and second holes overlap.

22. The method of claim 21, further comprising directing a dilator into the overlapping first and second holes to create a cavity in the wall of the femoral notch.

23. The method of claim 14, further comprising attaching a first portion of a ligament graft to the first hole when the knee is in a first position and attaching a second portion of the ligament graft to the second hole when the knee is in a second, substantially different position.

24. The method of claim 14, wherein inserting the first guidewire comprises inserting the first guidewire into the wall of the femoral notch through the first opening in the template, and inserting the second guidewire comprises inserting the second guidewire into the wall of the femoral notch through the second opening in the template.

25. The method of claim 14, wherein inserting the first guidewire comprises using the first opening in the template to mark a guidewire location and inserting the first guidewire using the marked guidewire location.

26. The method of claim 25, wherein inserting the second guidewire comprises using the second opening in the template to mark a second guidewire location and inserting the second guidewire using the marked second guidewire location.

27. The method of claim 25, wherein marking the guidewire location comprises using electro-cautery techniques.

28. A method of forming a cavity for cruciate ligament reconstruction surgery, the method comprising:

inserting a first guidewire into a femur;

inserting a second guidewire into the femur using a device configured to space the second guidewire a predetermined distance from a location defined by the first guidewire;

drilling a first hole in the femur using the first guidewire; and drilling a second hole in the femur using the second guidewire.

29. The method of claim 28, wherein the device comprises a template body including openings sized and positioned to receive the guidewires and to direct the guidewires into the wall of the femoral notch.

30. The method of claim 28, wherein drilling the first hole comprises drilling the first hole after inserting the first guidewire and before inserting the second guidewire.

31. The method of claim 30, wherein inserting the second guidewire comprises inserting the second guidewire using a device configured to space the second guidewire a predetermined distance from the first hole.

* * * * *